US 6,668,192 B1

(12) United States Patent
Parker et al.

(10) Patent No.: US 6,668,192 B1
(45) Date of Patent: Dec. 23, 2003

(54) AUTOMATED EXTERNAL DEFIBRILATOR WITH THE ABILITY TO STORE RESCUE INFORMATION

(75) Inventors: William S. Parker, Maple Grove, MN (US); Kenneth F. Olson, Edina, MN (US); Michael A. Tvedt, Savage, MN (US)

(73) Assignee: Cardiac Science, Inc., Minneapolis, MN (US)

( * ) Notice: Subject to any disclaimer, the term of this patent is extended or adjusted under 35 U.S.C. 154(b) by 0 days.

(21) Appl. No.: 09/057,044

(22) Filed: Apr. 8, 1998

Related U.S. Application Data

(60) Provisional application No. 60/042,755, filed on Apr. 8, 1997.

(51) Int. Cl.[7] .................................................. A61N 1/39
(52) U.S. Cl. .............................. 607/5; 607/59; 600/522
(58) Field of Search .......................... 607/5, 2, 6, 59; 600/522

(56) References Cited

U.S. PATENT DOCUMENTS

| 4,945,477 A | 7/1990 | Edwards |
| 5,549,115 A | 8/1996 | Morgan et al. |
| 5,680,864 A | 10/1997 | Morgan et al. |
| 5,683,423 A | 11/1997 | Post |
| 5,716,380 A | 2/1998 | Yerkovich et al. |

OTHER PUBLICATIONS

Sur VivaLink *AED Automatic External Defibrillator System,* SurVivaLink Brochure, Sur VivaLink Corporation, 4 pages, Nov. 1993.

*Primary Examiner*—Kennedy Schaetzle
(74) *Attorney, Agent, or Firm*—Patterson, Thuente, Skaar & Christensen, P.A.

(57) ABSTRACT

An automated external defibrillator (AED) includes the ability to store rescue information. The AED has a case for housing a power supply that is electrically connected to a circuit for generating a defibrillation pulse. The circuit is electrically connected to a pair of electrodes that are applied to a patient to deliver the defibrillation pulse. The AED further comprises an archival storage means for storing rescue information. The archival storage means is containable within the case and is able to store various types of rescue information including patient data, operational data of the AED, and sound that occurs within the immediate vicinity of the AED during a rescue.

42 Claims, 5 Drawing Sheets

US 6,668,192 B1

AUTOMATED EXTERNAL DEFIBRILATOR WITH THE ABILITY TO STORE RESCUE INFORMATION

RELATED APPLICATION

This application claims the benefit of U.S. Provisional Application No. 60/042,755, filed Apr. 8, 1997, the contents of which are incorporated herein by reference.

TECHNICAL FIELD

The present invention relates generally to automated external defibrillators. In particular, the present invention is an automated external defibrillator (AED) with the ability to store rescue information including patient data, AED operational data and sound from a rescue event.

BACKGROUND OF THE INVENTION

Automated external defibrillators or AEDs are used by police officers, paramedics and other first-responder emergency medical technicians to resuscitate cardiac arrest patients. It is important that the AEDs carried by these technicians be continuously operational and ready for use on a moment's notice. It is essential that in a high stress situation of cardiac arrest, the technician be able to rely on the operability of the AED. Studies have shown that the chances of successfully resuscitating a patient decreases approximately ten percent per minute following cardiac arrest. Thus, it is vital to be able track and monitor the operation of the AED and its users through various rescue events so that appropriate and timely responses by the AED and its users may be ensured. There is, therefore, a need for an AED that has the ability to record rescue information including patient data, AED operational data and/or the sound from a rescue event.

SUMMARY OF THE INVENTION

The problems outlined above are in large measure solved by an automated external defibrillator (AED) with the ability to store rescue information. The AED has a case for housing a power supply that is electrically connected to a circuit for generating a defibrillation pulse. The circuit is electrically connected to a pair of electrodes that are applied to a patient to deliver the defibrillation pulse. The AED further comprises an archival storage means for storing rescue information. The archival storage means is containable within the case and is able to store various types of rescue information including patient data, operational data of the AED, and sound that occurs within the immediate vicinity of the AED during a rescue.

DETAILED DESCRIPTION OF THE DRAWINGS

Figure 1:
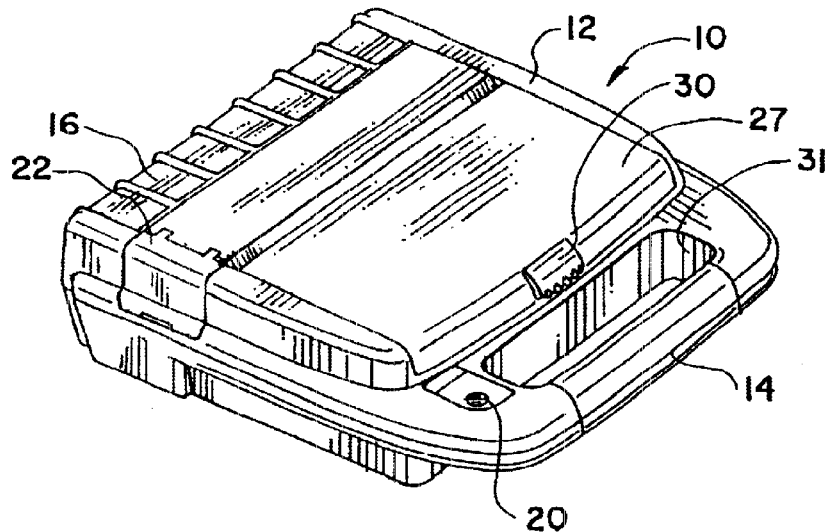
FIG. 1 is a perspective view of an automated external defibrillator (AED)
Figure 2:
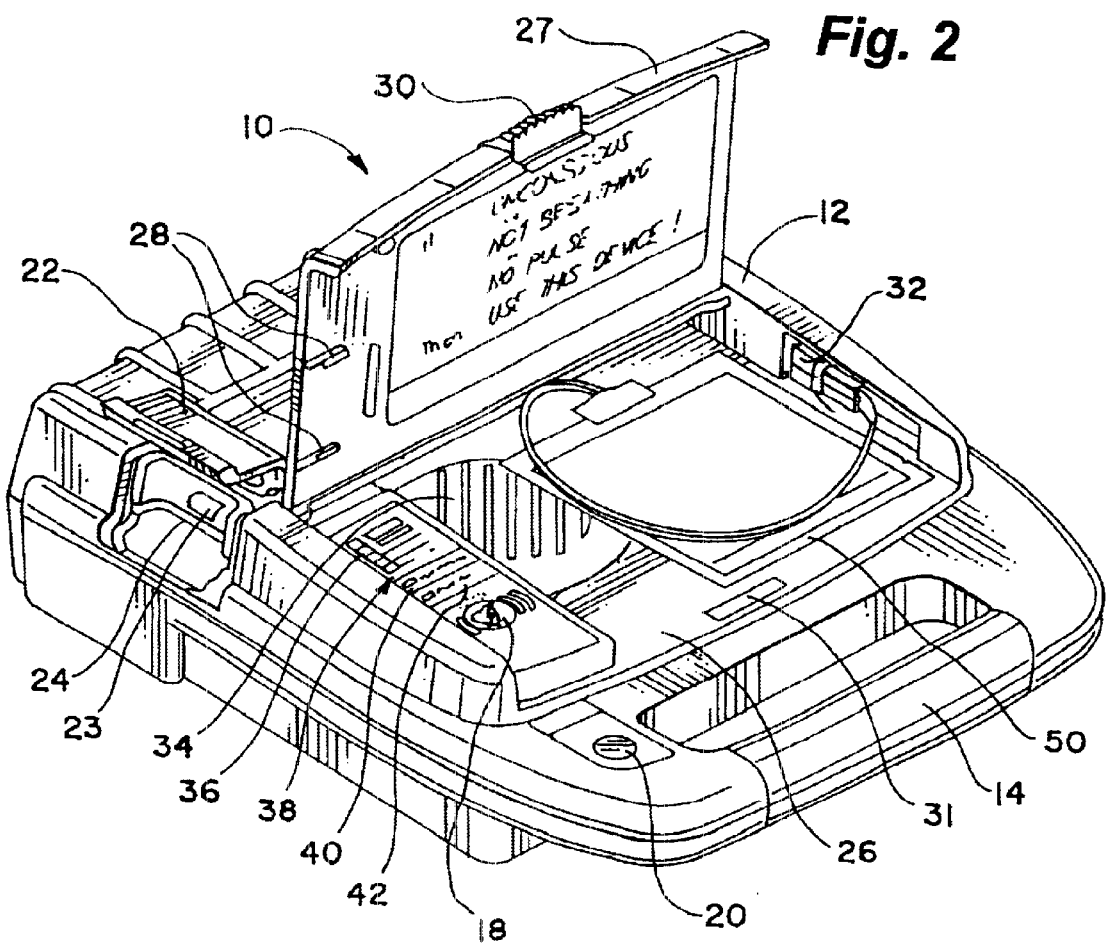
FIG. 2 is a perspective view of the AED of FIG. 1 having the lid opened.

Referring to FIGS. 1–5, an automated external defibrillator (AED) 10 with the ability to store rescue information may be appreciated. The stored rescue information may include patient data, AED operational data and/or sound.

As shown AED 10 includes a plastic case 12 with a carrying handle 14 on the front portion. A battery compartment (not visible) in the rear portion of AED 10 is enclosed by a battery pack 16, the battery pack 16 being removably disposed within the battery compartment. A visual maintenance indicator 20, and a data access door 22 concealing a serial connector port 23 and a data card slot 24, are located on the outside of case 12 for easy access by an operator.

Figure 4:
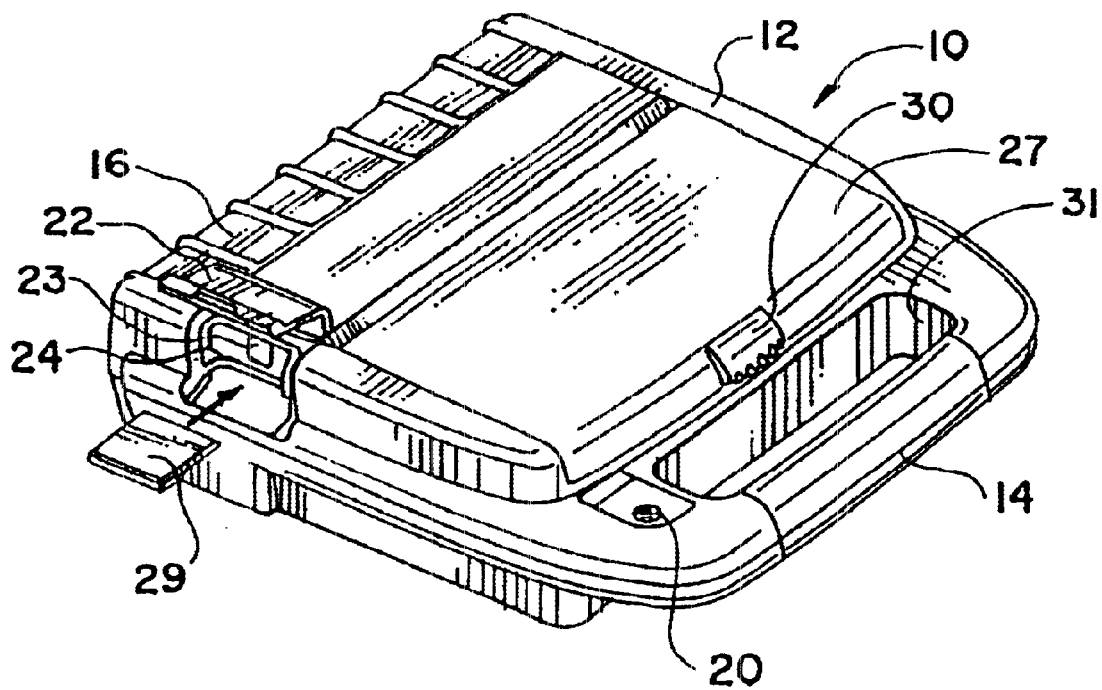
FIG. 4 is a perspective view of the AED having the rescue information data card being inserted therein according to the present invention.

Case 12 also includes an electrode compartment 26 defined in the top portion of the case 12. An illuminatable resume/rescue switch 18 (depicted in FIG. 2) is disposed adjacent to the electrode compartment 26. The electrode compartment 26 is enclosed by lid 27 which is mounted to the case 12 by hinges (not visible). The lid 27 covers the resume/rescue switch 18 when the lid 27 is in the closed disposition, as depicted in FIGS. 1 and 4. The resume/rescue switch 18 is actually a single switch with illuminatable labels alternatively indicating the "resume" or the "rescue" function, "rescue" appearing above the switch 18 and "resume" appearing below the switch 18, depending on whether the AED 10 is cuing the operator to perform a rescue or resume operation by activating the switch 18.

Figure 3:
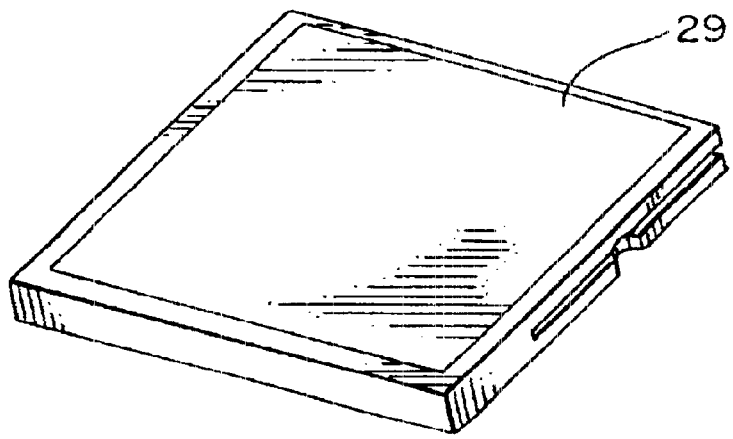
FIG. 3 is a perspective view of a rescue information data card.

The inside of lid 27 incorporates a data card storage clasp 28 for holding a data card 29 (depicted in FIG. 3). A bayonet-type releasable latch 30 holds lid 27 closed when AED 10 is not in use by engaging a receiving recess 31 defined in the floor of the electrode compartment 26. The lid 27 is opened by grasping the underside of the latch 30, pushing in and lifting upward on the latch 30 to gain access to the electrode compartment 26.

An electrode connector 32, speaker 34 and diagnostic display panel 36 are located on case 12 within the electrode compartment 26. The diagnostic display panel 36 is disposed adjacent to the illuminatable rescue switch 18. Diagnostic display panel 36 includes visual "Battery Status" indicator light 38, "Electrodes" indicator light 40, and "Service" indicator light 42. An instruction and safety label is located in the inside surface of electrode compartment lid 27. Electrodes 50 are removably connected to electrode connector 32. Electrodes 50 typically include a pair of electrodes for attachment to a patient in a sealed package.

Figure 5:
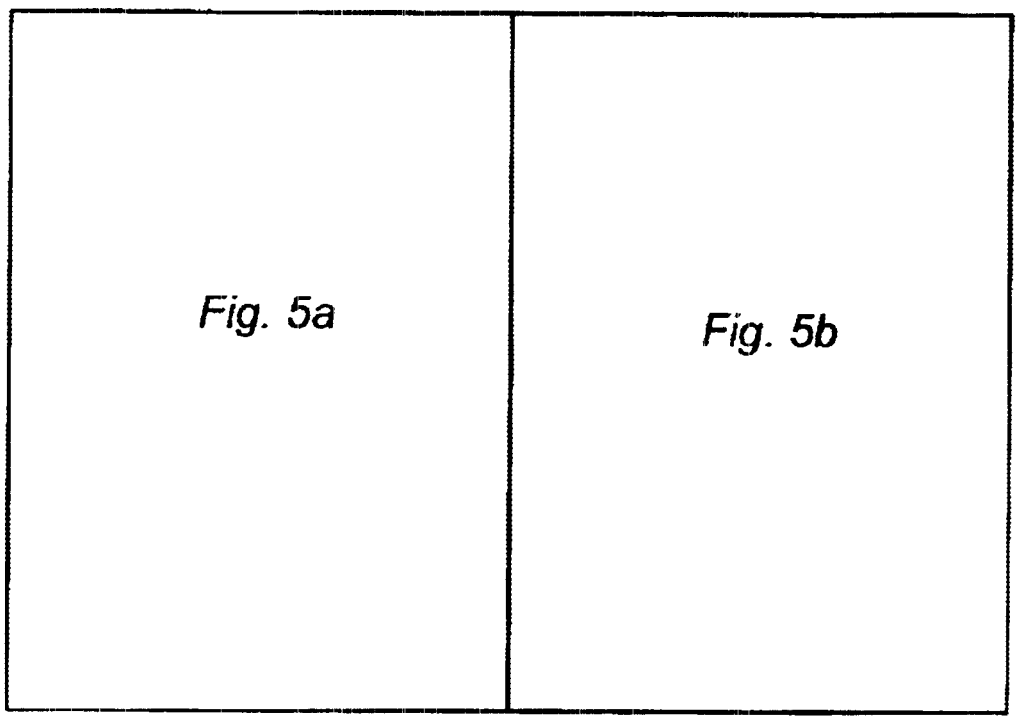
FIG. 5 is a block diagram of an electrical system of the AED.
Figure 5A:
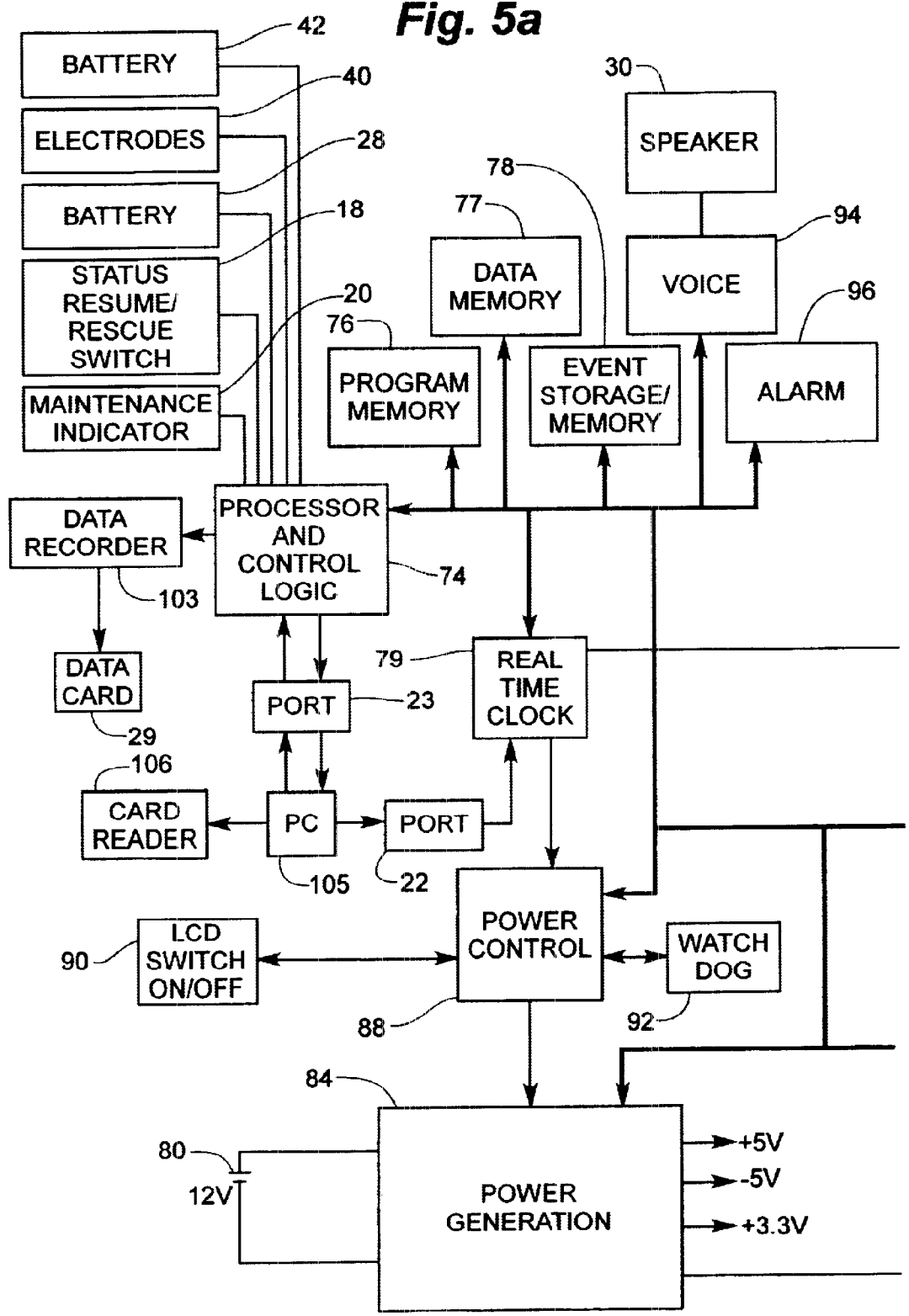
Figure 5B:
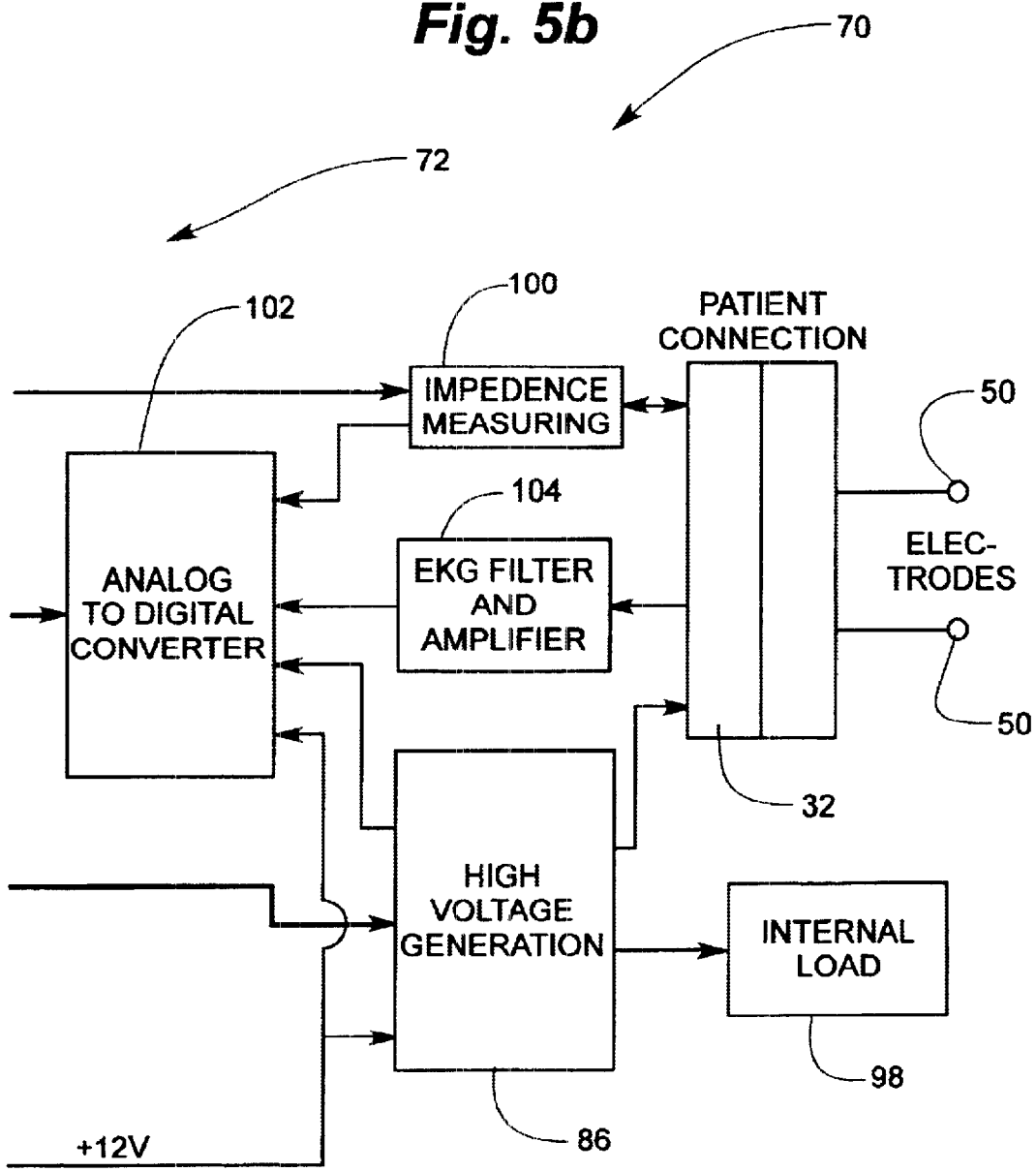

FIG. 5 is a block diagram of the electrical system 70 of AED 10. The overall operation of AED 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program. Electrical power is preferably provided by a lithium sulphur dioxide battery 80 which is enclosed in the battery pack 16, the battery pack 16 being removably positioned within the battery compartment. the battery 80 may be comprised of a plurality of battery cells that are electrically coupled together. The battery 80 is connected to power generation circuit 84. The "Battery Status" indicator light 38 will indicate the charge status of the battery 80 and prompt the operator to replace the battery 80 when needed.

During normal operation, power generation circuit 84 generates regulated ±5V and 12V (actually about 5.4V and 11.6V) supplies with the power provided by the battery 80. The ±5V output of the battery 80 functions as a back-up battery to power components of electrical system 70 during the execution of self-tests and to activate maintenance indicators and alarms (as described below). Although not separately shown in FIG. 5, power generation circuit 84 includes voltage level sensing circuits which are coupled to processor 74. The voltage level sensing circuits provide low battery level signals to processor 74.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment, and provides signals to processor 74 indicating whether lid 27 is open or closed. Serial connector port 23 is coupled to processor 74 for two-way serial data transfer using an RS-232 protocol. Resume/rescue switch 18 and the "rescue" and "resume" indications thereof, maintenance indicator 20, and the "Battery Status" indicator light 38, "Electrodes" indicator light 40, and "Service" indicator light 42 of the diagnostic display panel 36, voice circuit 94 and piezoelectric audible alarm 96 are also connected to processor 74. Voice circuit 94 is connected to the speaker 34. In response to voice prompt control signals from processor 74, circuit 94 and speaker 34 generate audible voice prompts.

High voltage generation circuit 86 is also connected to and controlled by processor 74. High voltage generation circuit such as circuit 86 are generally known, and disclosed, for example, in the commonly assigned Persson et al., U.S. Pat. No. 5,405,361, which is hereby incorporated by reference. In response to charge control signals provided by the processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to the high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from the electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). If the conductive adhesive on electrodes 50 is dried out, electrodes 50 are not properly connected to connector 32, or electrodes 50 are not properly positioned on the patient, a relatively high resistance (e.g, greater than about one hundred ohms) will be present across the connector 32. The resistance across connector 32 will be between about fifty and eighty ohms when fresh electrodes 50 are properly positioned on the patient with good electrical contacts. The impedance signal representative of the impedance measured by circuit 100 is digitized by A/D converter 102 and provided to processor 74.

AED 10 also includes a data recorder 103 that is interfaced to processor 74 and positioned internally within AED 10 adjacent data card slot 24 so as to be ready to accept data card 29. AED 10 further includes an electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of AED 10 is initiated when an operator opens lid 27 to access the electrodes 50. The opening of the lid 27 is detected by lid switch 90, which effectively functions as an on/off switch. In response to this action, power control circuit 88 activates power generation circuit 84 and initiates rescue mode operation of processor 74. Processor 74 then begins its rescue mode operation by switching maintenance indicator 20 to a maintenance required state (e.g., a yellow visual display in one embodiment), flashing rescue switch light associated with the resume/rescue switch 18 and the indicator lights on diagnostic display panel 36, and performing a lid opened self-test.

During the lid opened self-test, processor 74 checks: 1) the charge state of battery 80; 2) the interconnection and operability of electrodes 50; 3) the state of event memory 78; 4) the functionality of real time clock 79; and 5) the functionality of A/D converter 102. The charge state of battery 80 is checked by monitoring the voltage level signals provided by power generation circuit 84. If battery 80 is determined to have a low charge, the "battery status" indicator on diagnostic display panel 36 will indicate the sensed status. The interconnection and operability of the electrodes 50 are checked by monitoring the impedance signals provided by impedance measuring circuit 100. If the electrodes 50 are missing or unplugged from connector 32, or if the electrodes 50 are damaged, processor 74 will illuminate the "Electrodes" indicator light 40 on diagnostic display panel 36.

Further, during the lid opened self-test, processor 74 accesses the event memory 78 to determine whether data from a previous rescue is still stored in memory. If so, processor 74 causes the "resume" indicator associated with the resume/rescue switch 18 on diagnostic panel 36 to be illuminated, and initiates the generation of a "Press resume button to clear memory and continue" voice prompt. If resume/rescue switch 18 is pressed by the operator following the activation of these indicators, processor 74 clears event memory 78 and proceeds with its rescue mode operation. The functionality of real time clock 79 and A/D converter 102 are checked by monitoring the outputs of these circuit elements for expected signals. Diagnostic display panel light 38 is illuminated by processor 74 if faults are identified in either of real time clock 79 or A/D converter 102.

If the lid opened self-test is successfully completed, processor 74 switches maintenance indicator 20 to an operational state and initiates the rescue mode of operation of AED 10. The rescue mode of operation generates audible voice prompts to guide the user through the operations of AED 10 and if necessary, delivery of a defibrillation pulse. The AED 10 determines its rescue mode steps of operation by monitoring the impedance across electrode connector 32 and by monitoring the patient's cardiac rhythm.

The closing of lid 27 after rescue mode operation activates processor 74 to initiate and perform a lid closed self-test. During the lid closed self-test processor 74 performs a comprehensive check of the status and functionality of AED 10, including: 1) the state of event memory 78, 2) the functionality of real time clock 79; 3) the functionality of A/D converter 102; 4) the functionality of program memory 76, data memory 77 and event memory 78; 5) the charge state of battery 80; and 6) the interconnection and operability of electrodes 50. The state of event memory 78, the state of battery 80, the interconnection and operability of electrodes 50, and the functionality of real time clock 79 and A/D converter 102 are checked in a manner identical to that described above with reference to the lid opened self-test.

Conventional memory test routines are implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery 80 or the interconnection or functionality of electrodes 50 during the lid closed self test.

A daily self-test is initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 switches maintenance indicator 20 to its maintenance required state if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to an internal resistive load 98. While the high voltage generation circuit 86 is operating in the charge mode, processor 74 monitors the time required to charge the circuit's capacitors and the capacitor voltage. A fault is identified if either is out of nominal conditions. Maintenance indicator 20 and alarm 96 are actuated in the manner described above if any faults are identified during the weekly self-test. Note that all performed test and patient data may be recorded in event memory 78.

Watch dog timer 92 is set to time watch dog time-out periods of about thirty hours (i.e., a period greater than twenty-four hour periods between daily self-tests), and is reset by processor 74 at the beginning of each daily self-test and each time lid 27 is opened. In the event control system 70 malfunctions and watch dog timer 92 times out, power control circuit 88 causes processor 74 to switch maintenance indicator 20 to the maintenance required state and to actuate alarm 96 to alert an operator to the fact that AED 10 requires maintenance.

AED 10 facilitates archival storage of rescue information in that data representative of the operation of AED 10, patient data, including the monitored cardiac rhythm of the patient, AED analysis of the patient data, key events detected during the rescue operation, and sound occurring within the immediate vicinity of AED 10 are stored in event memory 78 during rescue mode operation. However, if data card 29, which is preferably a memory card commonly known as a flashcard, is inserted into card slot 24 before beginning the rescue attempt, the rescue information is automatically recorded by data recorder 103 onto data card 29 thereby also facilitating archival storage of rescue information. The data card 29 is preferably a memory card having a RAM storage capability of 2, 4, 8, 10, or 15 megs capacity.

Data card 29 is capable of storing up to twenty minutes of rescue information and sound. With data card 29 inserted, the default settings of AED 10 are such that sound is automatically recorded. The sound recording capability may be disabled, however thereby extending the time that rescue information may be recorded on data card 29 up to five hours.

Note that if data card 29 is inserted containing previously stored rescue data, a voice prompt will be issued that says "Card full. Storing internally." If upon hearing this prompt, the operator ejects the full data card 29 and inserts an empty data card 29 before placing electrodes 50 on the patient, rescue data will then be stored on the new card 29. If full card 29 is left in slot 24 when electrodes 50 are placed on the patient, rescue information will then be stored in AED event memory 78.

Stored data representative of the operation of AED 10 includes the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86, and 5) the actuation of the resume/rescue switch 18 in the rescue mode. The actual time base of the patient's cardiac rhythm, e.g., EKG information, is also stored.

Following a rescue, the stored data can be retrieved from event memory 78 through the use of a personal computer (PC) 105 interfaced to serial connector port 23. Real time clock 79 can also be set through the use of PC 105 interfaced to communications port 22. If the stored data were stored on data card 29 and data card 29 remains in slot 24, the data may also be retrieved through the use of PC 105 interfaced to serial connector port 23. Alternatively, the data card 29 may be ejected from AED 10 and inserted into an appropriate card reader 106 that is directly connected to PC 105, such as a PCMCIA type I card reader.

In the event that PC 105 does not have a card reader, the card reading hardware of the AED 10 may be used to provide the data card reading function for the PC 105. This is accomplished by interfacing PC 105 to serial connector port 23 of the AED 10. This is typically accomplished by connecting a multi-strand wire (not shown) to the PC 105 and the serial connector port 23. The datacard 29 is then inserted into slot 24 of the AED 10 to establish a communications interface between the datacard 29 and the processor 74. When this accomplished, the software of the PC 105 can access the information stored on the data card 29, as the processor 74 configures the AED 10 to provide the card reading function for the PC 105.

PC 105 may be used to clear event memory 78 and/or data card 29 of previous rescue information when PC 105 is connected to AED 10 through serial connector port 23. The data card reader 106 of PC 105 may also be used to clear the memory of data card 29. Once rescue information is retrieved from event memory 78 or data card 29 by PC 105, PC 105 may be used to enter additional information to help identify the rescue information. This additional information may include patient name, medical identification, name of the responder who performed the rescue and the serial number of AED 10. PC 105 can be used to display all data to the user and to keep logs of performance.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the twenty most recently performed tests are stored in memory 78. The stored self-test records can be retrieved from memory 78 through PC 105 interfaced to serial connector port 23.

AED 10 offers considerable advantages in that it allows recordation and thus, tracking of the operation of AED 10, of patient data and of actual sound from a rescue event occurring within the immediate vicinity of AED 10. Such data may be used to evaluate performance of the AED 10 itself as well as the performance of the responder that is using the AED 10. Further, the information tracking may be used to develop new features for AED 10 and new methods for training users of AED 10.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. An automated external defibrillator (AED) with the ability to store rescue information, the AED having a case for housing a power supply that is electrically connected to a circuit for generating a defibrillation pulse and wherein the circuit is electrically connected to a pair of electrodes that are applied to a patient to deliver the defibrillation pulse, comprising:

an archival storage means for storing rescue information, said archival storage means containable within said case, wherein said archival storage means comprises a data card designed to be insertable in a data card reader of a personal computer and wherein said personal computer is designed to retrieve the stored rescue information from the inserted data card and for entry of additional information to identify the retrieved rescue information and to log the retrieved rescue information;

wherein the rescue information comprises patient data, AED analysis of the patient data, operational data of the AED and key events detected during a rescue operation, and sound occurring within the immediate vicinity of the AED, and wherein the AED is designed to provide audible notification when the inserted data card is full of previously stored rescue information.

2. The AED of claim 1, wherein said data card is a RAM memory card having a RAM storage capacity selected from a list of capacities consisting of:

2 megs;
4 megs;
8 megs;
10 megs; and
15 megs.

3. The AED of claim 1, wherein the AED further comprises a lid attached to the case, said lid having a data card storage clasp for holding said data card.

4. The AED of claim 1, wherein the AED further comprises a lid attached to the case and wherein said archival storage mean automatically begins storing the rescue information upon opening of said lid.

5. An automated external defibrillator (AED) with the ability to store rescue information, the AED having a case for housing a power supply that is electrically connected to a circuit for generating a defibrillation pulse and wherein the circuit is electrically connected to a pair of electrodes that are applied to a patient to deliver the defibrillation pulse, comprising:

an archival storage system comprising a processor internal to the case and a data card that is removably, insertable within the case, the inserted data card communicatively interfaced to said processor wherein said processor directs storage of the rescue information to the inserted data card;

wherein the rescue information comprises patient data that is obtainable during a rescue, operational data of the AED that is obtainable during the rescue, and sound occurring within the immediate vicinity of the AED that is obtainable during the rescue, and wherein the AED is designed to provide audible notification when the interfaced data card is full of previously stored rescue information.

6. The AED of claim 5, wherein said removably, instertable data card is a two, four, eight or ten mega RAM memory card.

7. The AED of claim 5, wherein the AED further comprises a lid attached to the case, said lid having a data card storage clasp for holding said data card.

8. The AED of claim 5, wherein the AED further comprises a lid attached to the case and wherein said archival storage system automatically being storing the rescue information upon opening of said lid.

9. The AED of claim 5, wherein said removably, insertable data card is designed to be insertable within a data card reader of a personal computer and wherein said personal computer is designed to retrieve the stored rescue information from the inserted data card.

10. The AED of claim 9, where said personal computer is designed for entry of additional information to identify the retrieved rescue information and to log the retrieved rescue information.

11. The AED of claim 9, wherein said removably, insertable data card is a RAM memory card having a RAM storage capacity selected from a list of capacities consisting of:

2 megs;
4 megs;
8 megs;
10 megs; and
15 megs.

12. An automated external defibrillator (AED) with the ability to store rescue information, the AED having a case, comprising:

an archival storage system comprising a processor internal to the case, a data card that is removably, insertable in the case and a memory internal to the case, the inserted data card and said memory communicatively interfaced to said processor, wherein said processor directs storage of the rescue information to the inserted data card unless the inserted data card is full wherein said processor directs storage of the rescue information to said memory.

13. The AED of claim 12, wherein the rescue information comprises sound occurring within the immediate vicinity of the AED.

14. The AED of claim 13, wherein the rescue information further comprises patient data and operational data of the AED.

15. The AED of claim 12, wherein the AED further comprises a lid attached to the case, said lid having a data storage clasp for holding said data card.

16. The AED of claim 12, wherein the AED further comprises a lid attached to the case and wherein said archival storage system automatically begins storing the rescue information upon opening of said lid.

17. The AED of claim 12, wherein the AED is designed to provide audible notification when the inserted data card is full of previously stored rescue information.

18. The AED of claim 12, wherein the AED further comprises a serial port communicatively interfaced to said archival storage system and wherein said serial port is used in transferring the stored rescue information to a personal computer when the personal computer is communicatively coupled to the serial data port.

19. The AED of claim 18, wherein the AED is configured to provide personal computer access to a data card when the personal computer is communicatively coupled to the serial data port, the data card being communicatively coupled to an AED microprocessor.

20. The AED of claim 19, wherein said personal computer is designed for entry of additional information to identify the retrieved rescue information and to log the retrieved rescue information.

21. The AED of claim 12, wherein said removably, insertable data card is designed to be insertable within a data card reader of a personal computer and wherein said personal computer is designed to retrieve the stored rescue information from the inserted data card.

22. An automated external defibrillator (AED) with the ability to store rescue information, the AED having a case for housing a power supply that is electrically connected to a circuit for generating a defibrillation pulse and wherein the circuit is electrically connected to a pair of electrodes that are applied to a patient to deliver the defibrillation pulse, comprising:
   an archival storage means for storing rescue information, said archival storage means containable within said case;
   wherein the archival storage means comprises a data card, the data card being insertable in a data card reader of a personal computer, and the personal computer is designed to retrieve the stored rescue information from the inserted data card; and
   wherein the personal computer is designed for entry of additional information to identify the retrieved rescue information and to log the retrieved rescue information, and the AED is designed to provide audible notification when the inserted data card is full of previously stored rescue information.

23. An automated external defibrillator (AED) with the ability to store rescue information generated during treatment of a patient, the AED having a case for housing a power supply that is electrically connected to a circuit for generating a defibrillation pulse and wherein the circuit is electrically connected to a pair of electrodes that are applied to a patient to deliver the defibrillation pulse, comprising:
   an archival storage means for storing rescue information, said archival storage means containable within said case, wherein the AED is designed to provide an audible notification of remaining capacity of the archival storage means for storing rescue information.

24. The AED of claim 23, wherein the rescue information comprises patient data, AED analysis of the patient data, operational data of the AED and key events detected during a rescue operation, and sound occurring within the immediate vicinity of the AED.

25. The AED of claim 23, wherein said archival storage means comprises a memory internal to the AED.

26. The AED of claim 23, wherein said archival storage means comprises a data card.

27. The AED of claim 26, wherein said data card is a RAM memory card having a RAM storage capacity selected from a list of capacities consisting of:
   2 megs;
   4 megs;
   8 megs;
   10 megs; and
   15 megs.

28. The AED of claim 26, wherein the AED further comprises a lid attached to the case, said lid having a data card storage clasp for holding said data card.

29. The AED of claim 26, wherein said data card is designed to be insertable in a data card reader of a personal computer and wherein said personal computer is designed to retrieve the stored rescue information from the inserted data card.

30. The AED of claim 29, wherein said personal computer is designed for entry of additional information to identify the retrieved rescue information and to log the retrieved rescue information.

31. The AED of claim 23, wherein the AED further comprises a lid attached to the case and wherein said archival storage means automatically begins storing the rescue information upon opening of said lid.

32. The AED of claim 23, wherein the AED further comprises a serial port communicatively interfaced to said archival storage means and wherein said serial port is used in transferring the stored rescue information to a personal computer when the personal computer is communicatively coupled to the serial data port.

33. The AED of claim 32, wherein the AED is configured to provide personal computer access to a data card when the personal computer is communicatively coupled to the serial port, the data card being communicatively coupled to an AED microprocessor.

34. An automated external defibrillator (AED) with the ability to store rescue information, the AED having a case for housing a power supply that is electrically connected to a circuit for generating a defibrillation pulse and wherein the circuit is electrically connected to a pair of electrodes that are applied to a patient to deliver the defibrillation pulse, comprising:
   an archival storage system comprising a processor internal to the case and a data card that is removably, insertable within the case, the inserted data card communicatively interfaced to said processor wherein said processor directs storage of the rescue information to the inserted data card, wherein the AED is designed to provide an audible notification of remaining data card storage means storable capacity for storing rescue information.

35. The AED of claim 34, wherein the rescue information comprises patient data that is obtainable during a rescue, operational data of the AED that is obtainable during the rescue, and sound occurring within the immediate vicinity of the AED that is obtainable during the rescue.

36. The AED of claim 34, wherein said removably, insertable data card is a two- or four-mega RAM memory card.

37. The AED of claim 34, wherein the AED further comprises a lid attached to the case, said lid having a data card storage clasp for holding said data card.

38. The AED of claim 34, wherein the AED further comprises a lid attached to the case and wherein said archival storage system automatically begins storing the rescue information upon opening of said lid.

39. The AED of claim 34, wherein the AED further comprises a serial port communicatively interfaced to said archival storage system and wherein said serial port is used in transferring the stored rescue information to a personal computer when the personal computer is communicatively coupled to the serial data port.

40. The AED of claim 39, wherein the AED is configured to provide personal computer access to a data card when the personal computer is communicatively coupled to the serial data port, the data card being communicatively coupled to an AED microprocessor.

41. The AED of claim 39, wherein said removably, insertable data card is designed to be insertable within a data card reader of a personal computer and wherein said personal computer is designed to retrieve the stored rescue information from the inserted data card.

42. The AED of claim 39, wherein said personal computer is designed for entry of additional information to identify the retrieved rescue information and to log the retrieved rescue information.

* * * * *